(12) United States Patent
Wang et al.

(10) Patent No.: US 10,107,824 B2
(45) Date of Patent: Oct. 23, 2018

(54) METHOD FOR DETECTING CARDIOVASCULAR DISEASE BIOMARKER

(71) Applicant: National Tsing Hua University, Hsinchu (TW)

(72) Inventors: Yu-Lin Wang, Zhubei (TW); Gwo-Bin Lee, Hsinchu (TW); Shu-Chu Shiesh, Tainan (TW); Jen-Inn Chyi, Taoyuan (TW); Abiral Regmi, Hsinchu (TW); Indu Sarangadharan, Hsinchu (TW); Chen-Pin Hsu, Taipei (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 123 days.

(21) Appl. No.: 15/277,563

(22) Filed: Sep. 27, 2016

(65) Prior Publication Data

US 2017/0016916 A1  Jan. 19, 2017

Related U.S. Application Data

(63) Continuation-in-part of application No. 14/873,765, filed on Oct. 2, 2015.

(30) Foreign Application Priority Data

Apr. 20, 2015 (TW) ................... 104112606
Feb. 25, 2016 (TW) ................... 105105590

(51) Int. Cl.
*G01N 33/68* (2006.01)
*G01N 27/414* (2006.01)

(52) U.S. Cl.
CPC ..... *G01N 33/6893* (2013.01); *G01N 27/4145* (2013.01); *G01N 27/4146* (2013.01)

(58) Field of Classification Search
CPC .............. G01N 27/3271–27/3278; G01N 27/414–27/4148

(Continued)

(56) References Cited

U.S. PATENT DOCUMENTS

2006/0175205 A1   8/2006 Cui et al.
2007/0063304 A1 * 3/2007 Matsumoto ............ B82Y 10/00
                                                           257/462

(Continued)

FOREIGN PATENT DOCUMENTS

TW          201016591 A    5/2010
TW            I367325 B    7/2012
WO     WO 2013/048087 A2   4/2013

OTHER PUBLICATIONS

Lee et al., "Ion-Sensitive Field-Effect Transistor for Biological Sensing," Sensors, vol. 9, Sep. 7, 2009, pp. 7111-7131.

(Continued)

*Primary Examiner* — Bach T Dinh
(74) *Attorney, Agent, or Firm* — Birch, Stewart, Kolasch & Birch, LLP (57) ABSTRACT

A method for analyzing concentration of a cardiovascular disease (CVD) biomarker in a liquid sample includes: applying the liquid sample to a biosensor, the biosensor including a transistor having a drain, a source, and a gate terminal disposed between the gate and the source, and a reactive electrode spaced apart from the gate terminal of the transistor and having a receptor immobilized thereon for specific binding with the CVD biomarker, the liquid sample being in contact with the gate terminal and the reactive electrode; applying a voltage pulse between the reactive electrode and the source, the voltage pulse having a pulse width; monitoring a response current in response to the voltage pulse; and analyzing the response current.

11 Claims, 10 Drawing Sheets

(58) Field of Classification Search
USPC .................................... 204/403.01–403.15
See application file for complete search history.

(56) References Cited

U.S. PATENT DOCUMENTS

| | | | |
|---|---|---|---|
| 2007/0235346 A1 | 10/2007 | Popovich et al. | |
| 2008/0185295 A1* | 8/2008 | Briman | G01N 33/5438 |
| | | | 205/777.5 |
| 2008/0283875 A1* | 11/2008 | Mukasa | B82Y 10/00 |
| | | | 257/253 |
| 2010/0098585 A1 | 4/2010 | Chiu et al. | |
| 2012/0135540 A1* | 5/2012 | Bruno | G01N 33/5308 |
| | | | 436/501 |
| 2014/0154785 A1* | 6/2014 | Yun | G01N 33/54366 |
| | | | 435/287.1 |
| 2017/0037033 A1* | 2/2017 | Arora | C07D 403/14 |

OTHER PUBLICATIONS

Taiwanese Search Report, dated Jun. 20, 2017, for Taiwanese Application No. 105105590, as well as an English translation.
U.S. Appl. No. 14/870,563, filed Sep. 30, 2015.

* cited by examiner

METHOD FOR DETECTING CARDIOVASCULAR DISEASE BIOMARKER

CROSS-REFERENCE TO RELATED APPLICATIONS

This application is a continuation-in-part (CIP) of co-pending U.S. Patent Application Serial No. 14/873,765, which is filed on Oct. 2, 2015 and claims priority of Taiwanese Patent Application No. 104112606, filed on Apr. 20, 2015. This application also claims priority of Taiwanese Patent Application No. 105105590, filed on Feb. 25, 2016.

FIELD

The disclosure relates to a method for detecting analytes in a liquid sample, more particularly to a method for detecting a cardiovascular disease biomarker in a liquid sample.

BACKGROUND

The concentration of cardiovascular disease (CVD) biomarkers, such as troponin I and NT-proBNP, within human blood samples may be one of potential indices for diagnosis of acute congestive heart failure.

Conventional methods for detecting the CVD biomarkers in a liquid sample, such as Enzyme-Linked Immunosorbent Assay (ELISA) and the electrochemical redox method, are often time-consuming and have relatively low sensitivity. Moreover, such CVD biomarkers often exist in samples having relatively high ionic strength, such as human serum, leading to difficulty in detection due to a severe charge-screening effect.

SUMMARY

According to one aspect of the present disclosure, a method for analyzing concentration of a cardiovascular disease (CVD) biomarker in a liquid sample includes: applying the liquid sample to a bio sensor, the biosensor including a transistor having a drain, a source, and a gate terminal disposed between the gate and the source, and a reactive electrode spaced apart from the gate terminal of the transistor, the reactive electrode having a receptor immobilized thereon for specific binding with the CVD biomarker in the liquid sample, the liquid sample being in contact with the gate terminal of the transistor and the reactive electrode; applying a voltage pulse between the reactive electrode and the source of the transistor, the voltage pulse having a pulse width; monitoring a response current, which is produced in response to the voltage pulse, within the pulse width from the biosensor; and analyzing the response current that is correlated to the concentration of the CVD biomarker in the liquid sample.

BRIEF DESCRIPTION OF THE DRAWINGS

Other features and advantages of the disclosure will become apparent in the following detailed description of the embodiment (s) with reference to the accompanying drawings, of which.

DETAILED DESCRIPTION

Figure 1:
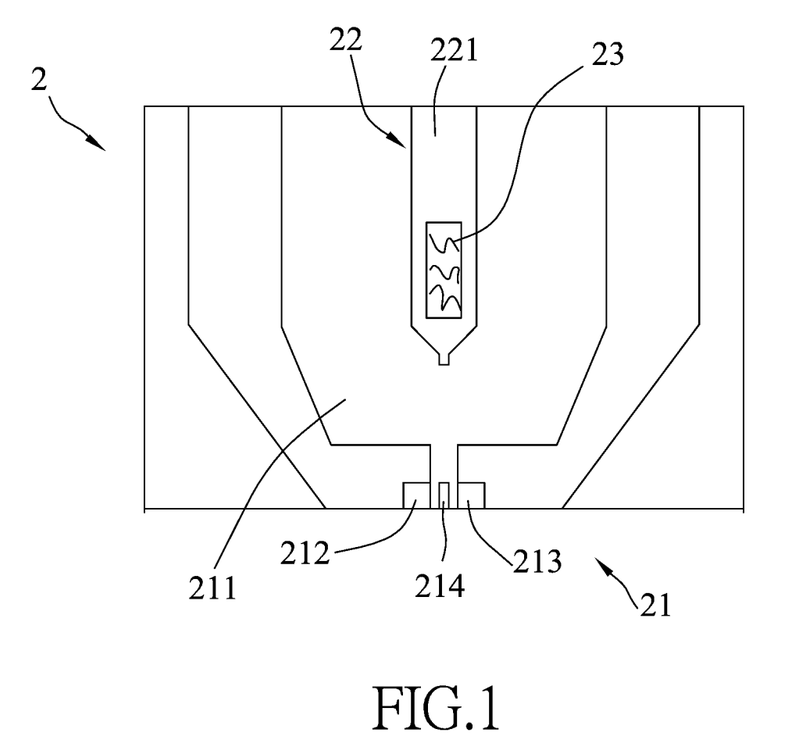
FIG. 1 is a top schematic view illustrating an exemplary embodiment of a biosensor for analyzing concentration of a CVD biomarker in a liquid sample according to the present disclosure.

Referring to FIG. 1, the exemplary embodiment of a biosensor 2 according to the present disclosure for analyzing concentration of a cardiovascular disease (CVD) biomarker in a liquid sample applied thereto includes a transistor 21 and a reactive electrode 22.

The transistor 21 has a substrate body 211, a source 212 formed on the substrate body 211, a drain 213 formed on the substrate body 211, and a gate terminal 214 that is disposed on the substrate body 211 and between the source 212 and the drain 213. The transistor 21 may be selected from the group consisting of a high electron mobility transistor (HEMT), a silicon-based transistor, a nanowire transistor, a carbon nanotube (CNT)-included transistor, a graphene transistor, and a molybdenum disulfide ($MoS_2$) transistor. In this embodiment, the transistor 2 is a HEMT, and the substrate body 211 has a GaN layer, and an AlGaN layer sequentially formed thereon.

The reactive electrode 22 is spaced apart from gate terminal 214 of the transistor 21 and is configured to contact with the liquid sample together with the gate terminal 214 of the transistor 21. As shown in FIG. 1, the reactive electrode 22 and the transistor 21 are integrally fabricated as a single piece in this embodiment (i.e., the substrate body 211 of the transistor 21 is extended to allow the reactive electrode 22 to be incorporated thereon). In this embodiment, the reactive electrode 22 has a surface metal layer 221 that has a receptor 23 immobilized thereon. The metal surface layer 221 of the reactive electrode 22 and the gate terminal 214 of the transistor 21 may be arranged in a coplanar manner. In this embodiment, the metal surface layer 221 of the reactive electrode 22 is made of gold, but the metal surface layer 221 may be made of other metals (e.g.,platinum), alloys or conductivematerials having affinity to biological molecules and thus should not be limited to the disclosure of this embodiment. The metal surface layer 221 of this embodiment may include gold nano-particles, which can be formed by chemical reduction, to further improve biological affinity of the reactive electrode 22. Since the technique of forming the gold nano-particles may be readily appreciated by those skilled in the art, further details will not be provided herein for the sake of brevity.

As illustrated in FIG. 1, the metal surface layer 221 of the reactive electrode 22 has the receptor 23 immobilized thereon for specific binding of the CVD biomarker. The receptor 23 may be an antibody or an aptamer. It should be noted that there is no other limitation on the selected receptor 23, so long as the receptor 23 can be immobilized on the metal surface layer 221 and facilitate specific binding with the CVD biomarker. In an embodiment where the metal surface layer 221 of the reactive electrode 22 is immobilized with the receptor 23.

A method for analyzing the CVD biomarker in the liquid sample utilizing the biosensor 2 of the exemplary embodiment according to the present disclosure includes Steps 200 to 204.

Step 200: applying the liquid sample to the biosensor 2. The liquid sample containing the CVD biomarker is applied onto the biosensor 2 in a manner that the gate terminal 214 of the transistor 21 and the metal surface layer 221 of the reactive electrode 22 are simultaneously in contact with the liquid sample. The liquid sample may be, but is not limited to, a buffer solution (e.g., tris-EDTA buffer or phosphate saline buffer) or a biological sample such as human blood, blood serum and blood plasma, etc. It should be noted that, when the liquid sample is a buffer solution, the liquid sample may be added with a reference protein, such as bovine serum albumin, to simulate the characteristics of human serum samples which contain the target CVD biomarker together with various background proteins having relatively high concentrations. The CVD biomarker in the liquid sample may specifically bind to the receptor 23 after a short period of time, for instance, 5 minutes, depending on the specie thereof.

Step 201: applying a voltage pulse to the liquid sample which is applied to the biosensor 2.

In Step 201 of this embodiment, the voltage pulse is applied between the reactive electrode 22 and the transistor 21. The applied voltage pulse has a pulse width that may not be greater than $10^{-3}$ second. Within such pulse width, the transient current response of the liquid sample at the biosensor 2 does not reach a steady state. In some embodiments, the pulse width may range from 2 µs to 100 µs. In some embodiments, the pulse width may range from 30 µs to 60 µs. In this embodiment, the amplitude of the voltage pulse is about 0.5 V, but is not limited thereto according to the present disclosure. It is worth noting that Step 201 can be conducted by a meter, an analyzer, a voltage generator and the like, and the biosensor 2 of this embodiment may be incorporated into a sensor strip.

It should be noted that, a working voltage may be applied between the source 212 and the drain 213 of the transistor 21 before the application of the voltage pulse, so as to enable the transistor 21 to have amplifying function. The working voltage may be in a range of 0.5 V to 10 V for enabling linear operation of the transistor 21.

Step 202: monitoring a response current within the pulse width of the voltage pulse from the source 212 of the transistor 21 of the biosensor 2. The application of the voltage pulse produces a response current that is in response to the voltage pulse due to the capacitance effect of the liquid sample between the reactive electrode 22 and the gate terminal 214 of the transistor 21 and that is amplified by the transistor 21. It should be noted that the response current may be monitored from either the source 212 or the drain 213 of the transistor 21 using a recorder or an analyzer, such as Agilent B1530A. It should also be noted that, in other embodiments, a response power, a response frequency, a response capacitance or a response impedance, which is in response to the voltage pulse, may be monitored and should not be limited to what is disclosed in this embodiment according to the present disclosure.

Step 203: analyzing the response current that is correlated to the concentration of the CVD biomarker in the liquid sample. The monitored response current can be analyzed using any suitable means, such as computers, analyzers or the like.

In one variation of this embodiment, when the liquid sample is added with a predetermined amount of the reference proteins, the method may further include a step of performing subtraction processing on the response current to subtract a reference response current contributed by solely the reference proteins provided in the liquid sample from the monitored response currents.

In one variation of this embodiment, the method may further include a step of performing integration computational processing on the response current with respect to at least a certain period in the pulse width in accordance with the following equation:

$$Q = I \times t$$

where a total charge (Q) accumulated at the biosensor 2 within the certain period in the pulse width (t) can be calculated from the response current (I). Such parameter obtained by performing the aforesaid integration computational processing may serve as an alternative or additional analyzing factor for analyzing the concentration of the CVD biomarker in the liquid sample.

By utilizing the reactive electrode 22, the biosensor 2 of the present disclosure is easy to fabricate, since immobilization of the receptor 23 on the reactive electrode 22 is relatively simple rather than immobilizing the same on the gate terminal 214 of the transistor 21. Moreover, by incorporating the transistor 21 and the reactive electrode 22 into the biosensor 2 of the present disclosure, the response current in response to the CVD biomarker concentration due to the capacitance effect between the metal surface layer 221 of the reactive electrode 22 and the gate terminal 214 of the transistor 21 may be amplified, so as to further lower the detection limit of the biosensor 2 according to the disclosure. Furthermore, by adopting the aforementioned method of the present disclosure, liquid samples having high salt concentrations, such as clinical human serum samples, can be directly analyzed using the biosensor 2 of the present disclosure without the need of being further diluted, i.e., the so-called charge-screening effect caused by high-concentration salt ions in the liquid sample can be avoided.

The following examples are for illustrating the exemplary embodiment only and should not be construed as limiting the scope of the present disclosure. In the description above, for the purposes of explanation, numerous specific details have been set forth in order to provide a thorough understanding of the embodiment(s).

EXAMPLES

<Immobilization of the Receptor>

Figure 2:
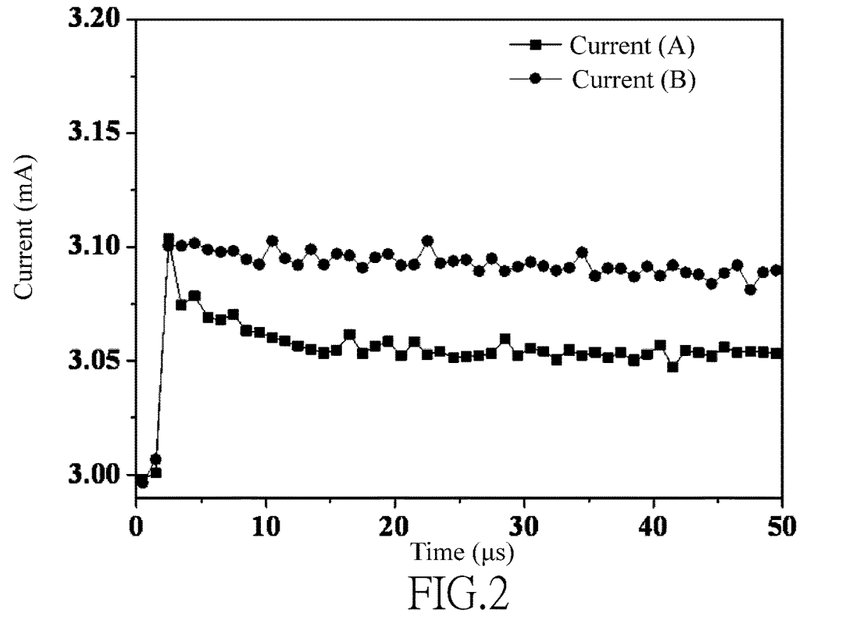
FIG. 2 shows plots of monitored response currents which are obtained respectively before and after an immobilization process of a receptor (within a BSA solution) onto a reactive electrode of the biosensor.

A phosphate buffer saline (PBS) buffer solution was applied dropwise onto the biosensor 2 of FIG. 1, so as to allow the metal surface layer 221 together with the gate terminal 214 of the transistor 21 contacted the PBS buffer solution. Thereafter, a working voltage of 0.5 V was applied to the transistor 21 while the source 212 of the transistor 21 was grounded. Thereafter, a voltage pulse having a pulse width of 50 μs and an amplitude of 0.5 V was applied to the reactive electrode 22 by an analyzer (Model: B1530/B1500A, commercially available from Agilent). A first response current (A) was measured accordingly from the source 212 of the transistor 21 and is illustrated in FIG. 2. After removing the PBS buffer solution, a solution containing NT-proBNP antibodies (i.e., the receptor 23, Product Name: Anti-NTpro-BNP, commercially available from Abcam) was applied dropwise onto the metal surface layer 221 of the reactive electrode 22, allowing the NT-proBNP antibodies to be immobilized thereon. Thereafter, the reactive electrode 22 and the transistor 21 were rinsed using phosphate buffer to remove non-binding NT-proBNP antibodies. The PBS buffer solution was then applied again to the reactive electrode 22 and the transistor 21 of the biosensor 2, and the same working voltage and the same voltage pulse was again applied to the biosensor 2, so as to obtain a second response current (B) as illustrated in FIG. 2. By comparing the first response current (A) and the second response current (B), immobilization of the NT-proBNP antibodies on the metal surface layer 221 of the reactive electrode 22 can be ascertained.

Example 1

Figure 3:
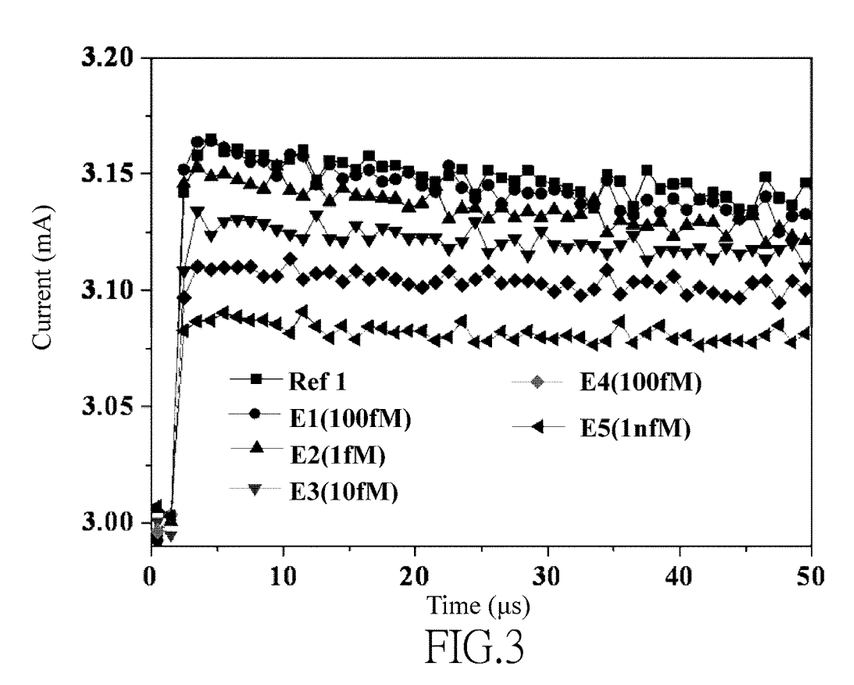
FIG. 3 shows plots of response currents of Examples 1 to 5 and Comparative Example 1 with respect to voltage pulse applying time.
Figure 4:
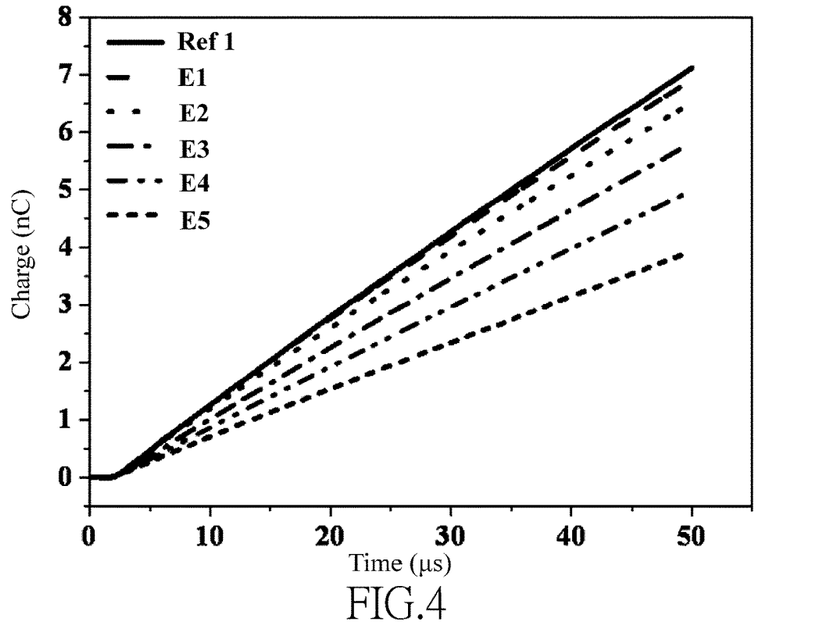
FIG. 4 shows the accumulated charges of Examples 1 to 5 and Comparative Example 1 with respect to the voltage pulse applying time.

A BSA/PBS buffer solution, containing 1% of BSA and serving as a reference protein solution, was applied onto the biosensor 2. A working voltage of 0.5V was first applied to the transistor 21 and a voltage pulse having a pulse width of 50 μs and an amplitude of 0.5 V was then applied between the reactive electrode 22 and the transistor 21 by the analyzer (Model: B1530/B1500A, commercially available from Agilent) 2 μs after the application of the working voltage, so as to obtain a response current of Reference 1. Subsequently, the BSA/PBS buffer solution was removed using an elution buffer, and a NT-proBNP solution (i.e., the liquid sample), containing 1% of BSA and NT-proBNP (i.e., the CVD biomarker) at a concentration of 100 fM, was applied onto the metal surface layer 221 of the reactive electrode 22 and the gate surface 214 of the transistor 21 for 5 minutes at 25° C. Thereafter, the same working voltage and the same voltage pulse were again applied to the biosensor 2 by the analyzer (Model: B1530/B1500A, commercially available from Agilent). A response current of Example 1 was monitored and is illustrated in FIG. 3. The total accumulated charge of Example 1 calculated by integrating the monitored response current over the voltage applying period is illustrated in FIG. 4.

Examples 2 to 5

The methods of Examples 2 to 5 were similar to that of Example 1, with the sole difference residing in that the liquid samples of Examples 2 to 5 have NT-proBNP concentrations of 1 pM, 10 pM, 100 pM, and 1 nM, respectively. The monitored response currents of Examples 2 to 5 are illustrated in FIG. 3, and the total accumulated charge of Examples 2 to 5 calculated respectively from the monitored response currents are illustrated in FIG. 4.

Example 6

Figure 6:
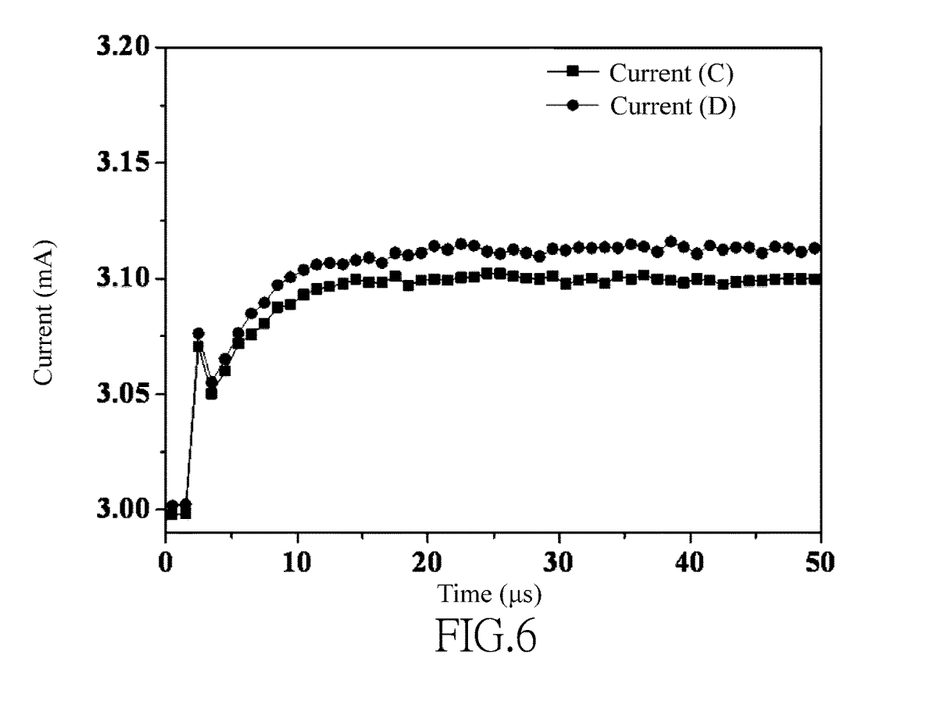
FIG. 6 shows plots of monitored response currents which are obtained before and after the immobilization process of the receptor (within a human serum solution) onto the reactive electrode of the biosensor.
Figure 7:
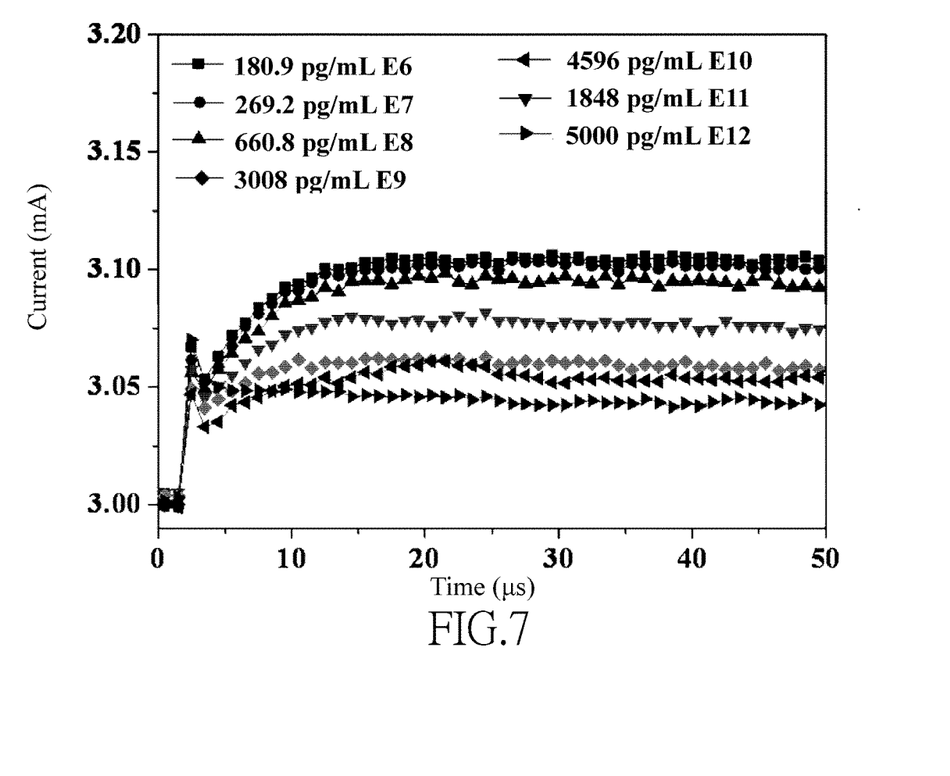
FIG. 7 shows plots of response currents of Examples 6 to 12 with respect to the voltage pulse applying time.

The method of Example 6 was similar to that of Example 1, with the differences residing as follows. In this example, a, and the results are shown in FIG. 6, where response currents (C), (D) were monitored before and after the immobilizing process of the NT-proBNP antibodies, respectively. Also, the liquid sample of Example 6 is a human serum sample containing 180.9 pg/ml of NT-proBNP, and the monitored response current thereof is illustrated in FIG. 7. The total accumulated charge calculated from the monitored response current of Example 6 is illustrated in FIG. 8.

Examples 7 to 12

The methods of Examples 7 to 12 were similar to that of Example 6, with the sole difference residing in that the liquid samples of Examples 7 to 12 have NT-proBNP concentrations of 269.2pg/ml, 660.8 pg/ml, 1848 pg/ml, 3008 pg/ml, 4596 pg/ml, and 5000 pg/ml, respectively.

Figure 8:
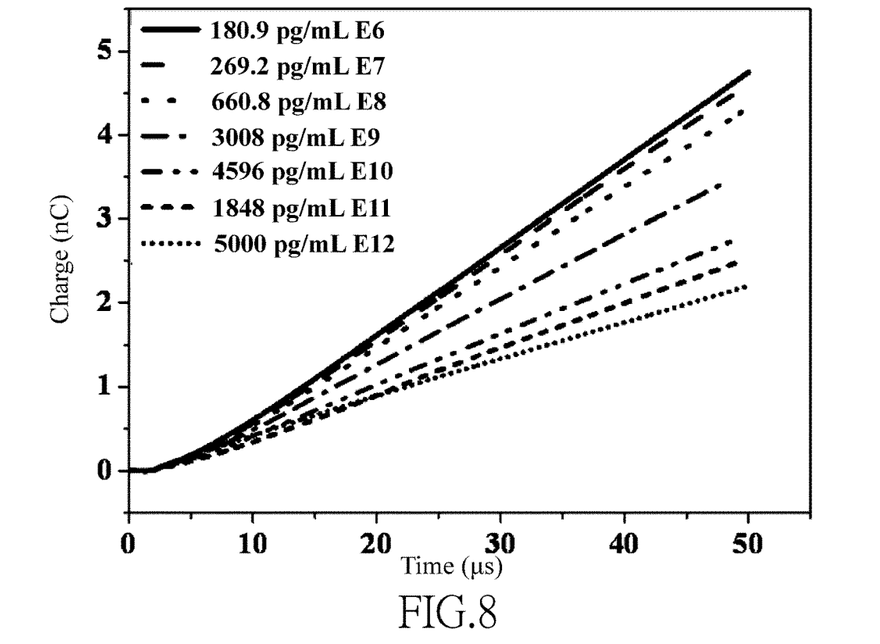
FIG. 8 shows the accumulated charges of Examples 6 to 12 with respect to the voltage pulse applying time.

The monitored response currents of Examples 7 to 12 are illustrated in FIG. 7, and the total accumulated charge calculated from the monitored response currents of Examples 7 to 12 are illustrated in FIG. 8.

Example 13

Figure 10:
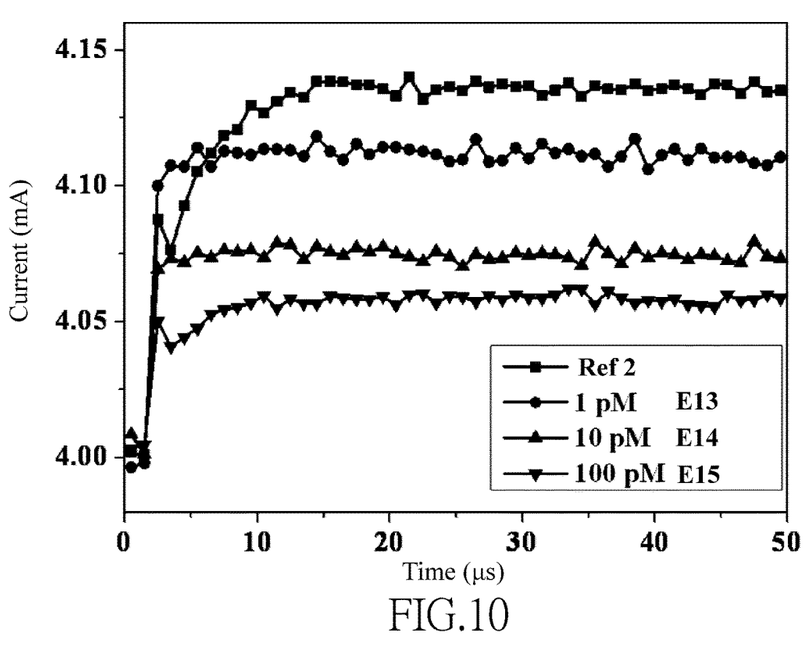
FIG. 10 shows plots of response currents of Examples 13 to 15 and Comparative Example 2 with respect to the voltage pulse applying time.
Figure 11:
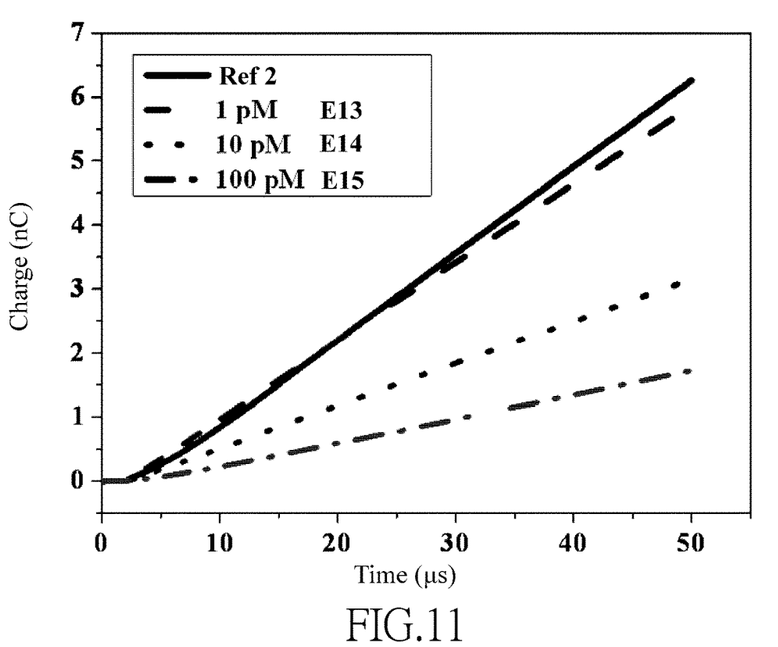
FIG. 11 shows the accumulated charges of Examples 13 to 15 and Comparative Example 2 with respect to the voltage pulse applying time.

The method of Example 13 was similar to that of Example 1, with the difference residing in that the liquid sample of Example 13 is a 1%BSA solution containing 1 pM of Troponin I (i.e., the CVD biomarker), and the receptor 23 is an Anti-cTnI antibody (Product Name: Anti-cTnI, commercially available from Abcom). The monitored response current of Reference 2 (i.e., the BSA reference solution) and the monitored response current of Example 13 are illustrated in FIG. 10. The total accumulated charge calculated from the monitored response current of Example 13 is illustrated in FIG. 11.

Examples 14 and 15

The methods of Examples 14 and 15 were similar to that of Example 13, with the sole difference residing in that the liquid samples of Examples 14 and 15 have Troponin-I concentrations of 10 pM and 100 pM, respectively. The monitored response currents of Examples 14 and 15 are illustrated in FIG. 10, and the total accumulated charge calculated from the monitored response currents of Examples 14 and 15 are illustrated in FIG. 11.

Examples 16 to 18

Figure 13:
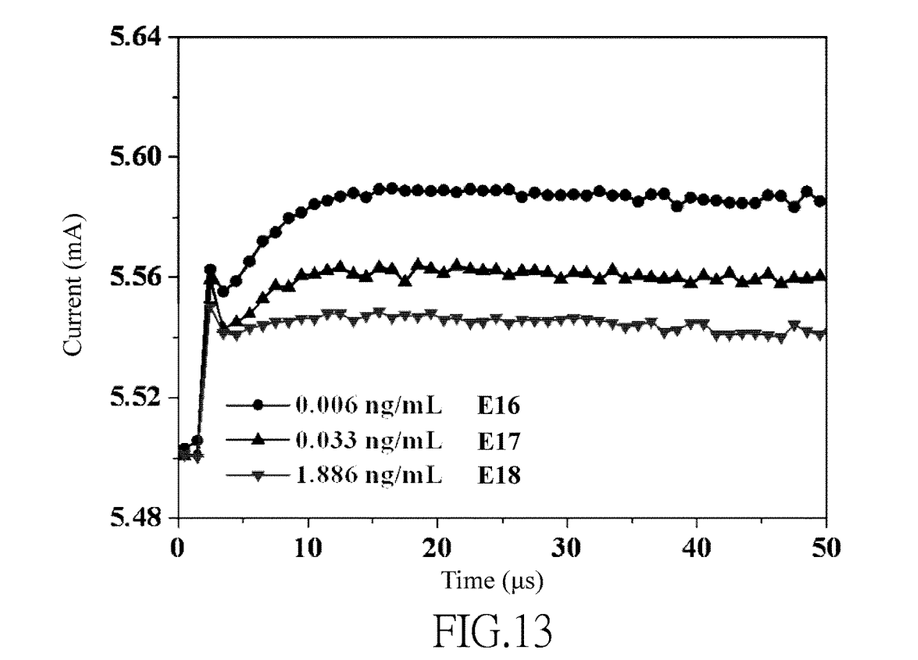
FIG. 13 shows plots of response currents of Examples 16 to 18 with respect to the voltage pulse applying time.
Figure 14:
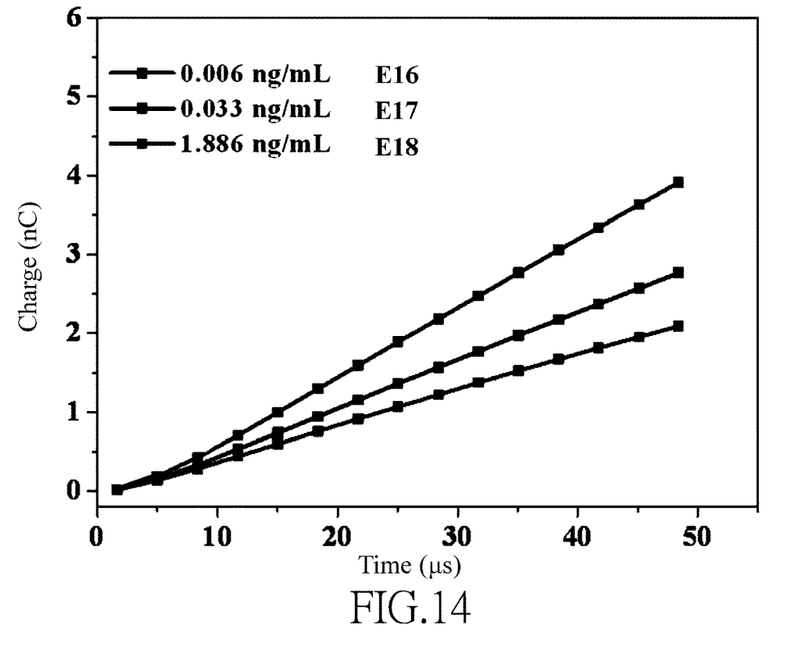
FIG. 14 shows the accumulated charges of Examples 16 to 18 with respect to the voltage pulse applying time.

The method of Examples 16 to 18 were similar to that of Example 13, with the sole difference residing in that the liquid samples of Examples 16 to 18 are human serum samples containing Troponin-I concentrations of 0.006 ng/ml, 0.033 ng/ml, and 1.886 ng/ml, respectively. The monitored response currents of Examples 16 to 18 are illustrated in FIG. 13, and the total accumulated charge calculated from the monitored response currents of Examples 16 to 18 are illustrated in FIG. 14.

Examples 19 to 21

Figure 16:
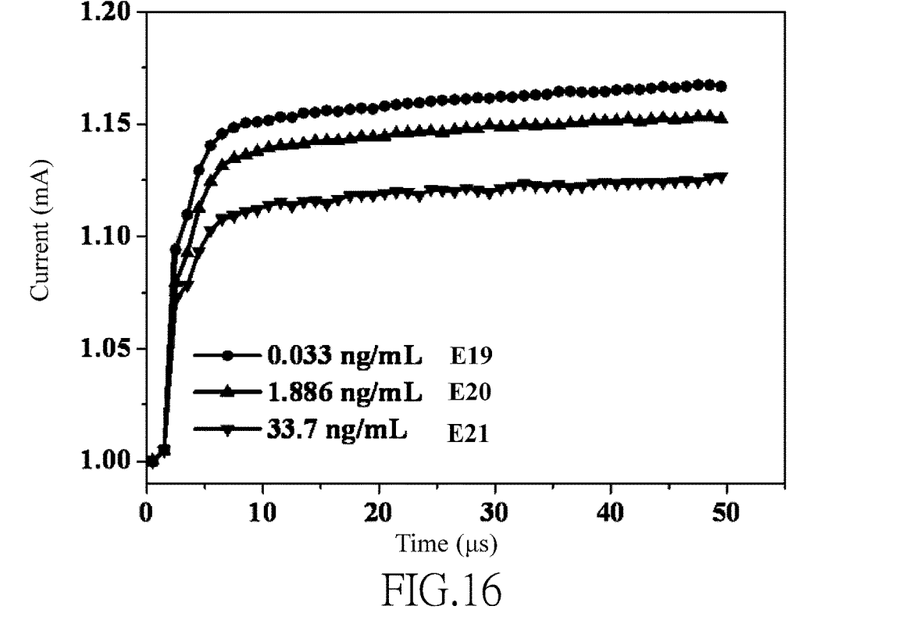
FIG. 16 shows plots of response currents of Examples 19 to 21 with respect to the voltage pulse applying time.
Figure 17:
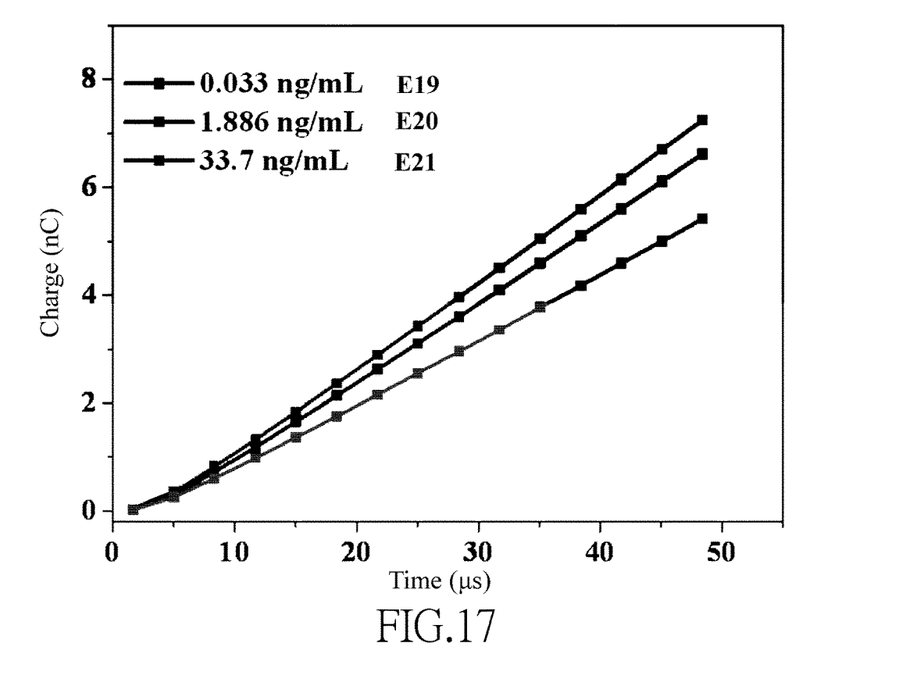
FIG. 17 shows the accumulated charges of Examples 19 to 21 with respect to the voltage pulse applying time.

The method of Examples 19 to 21 were similar to that of Example 16, with the sole difference residing in that the receptor 23 immobilized on the reactive electrode was an aptamer having a sequence of CGCATGCCAAACGTTGC-CTCATAGTTCCCTCCCCGTGTCC, and that the liquid samples of Examples 19 to 21 are human serum samples having Troponin-I concentrations of 0.033 ng/ml, 1.886 ng/ml, and 33.7 ng/ml, respectively. The monitored response current of Examples 19 to 21 are illustrated in FIG. 16, and the total accumulated charge calculated from the monitored response currents of Examples 19 to 21 are illustrated in FIG. 17.

[Data Analysis]

FIGS. 3, 7, 10, 13, and 16 correspondingly show plots of the response currents of Examples 1 to 21 and References 1 and 2 with respect to the voltage pulse applying time. It is clearly shown that the liquid samples with various CVD biomarker concentrations indeed have respective response currents under the same applied voltage pulse and the same working voltage. In addition, with the increasing CVD biomarker concentrations in the liquid samples, e.g., Examples 1 to 5 as shown in FIG. 3, the response current tends to decrease accordingly. Furthermore, with various CVD biomarkers in the liquid samples (e.g., the Examples correspondingly shown in FIGS. 3 and 10), with various types of the liquid sample (e.g., the Examples correspondingly shown in FIGS. 3 and 7), or with various receptors immobilized on the biosensor (e.g., the Examples correspondingly shown in FIGS. 13 and 16), the correlation between the response current and the CVD biomarker concentration in the liquid sample is substantially maintained. These results prove that the response current monitored within the pulse width of the voltage pulse is correlated to the analyte concentration in the liquid sample applied to the biosensor and can be utilized as a reliable analyzing factor.

Figure 9:
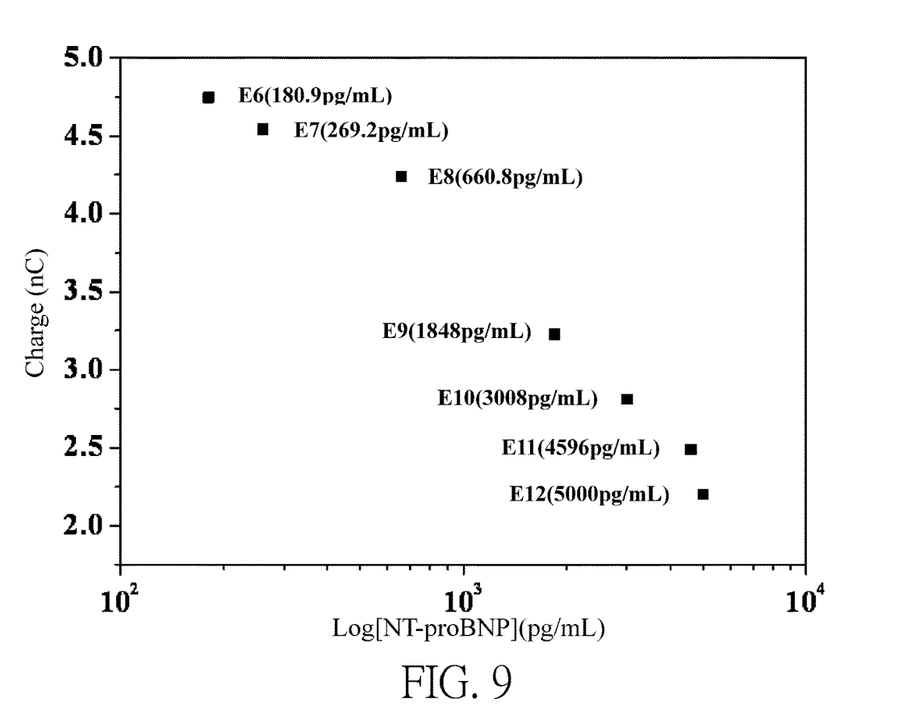
FIG. 9 shows the accumulated charges of Examples 6 to 12 at 50 μs after the application of the voltage pulse with respect to the CVD biomarker concentration in a logarithmic scale.
Figure 15:
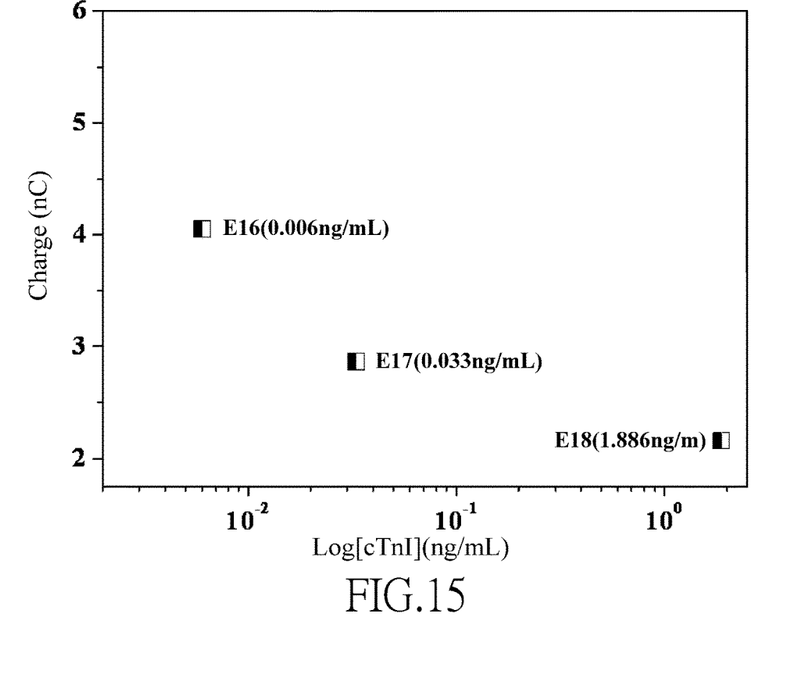
FIG. 15 shows the accumulated charges of Examples 16 to 18 at 50 μs after the application of the voltage pulse with respect to the CVD biomarker concentration in a logarithmic scale.
Figure 18:
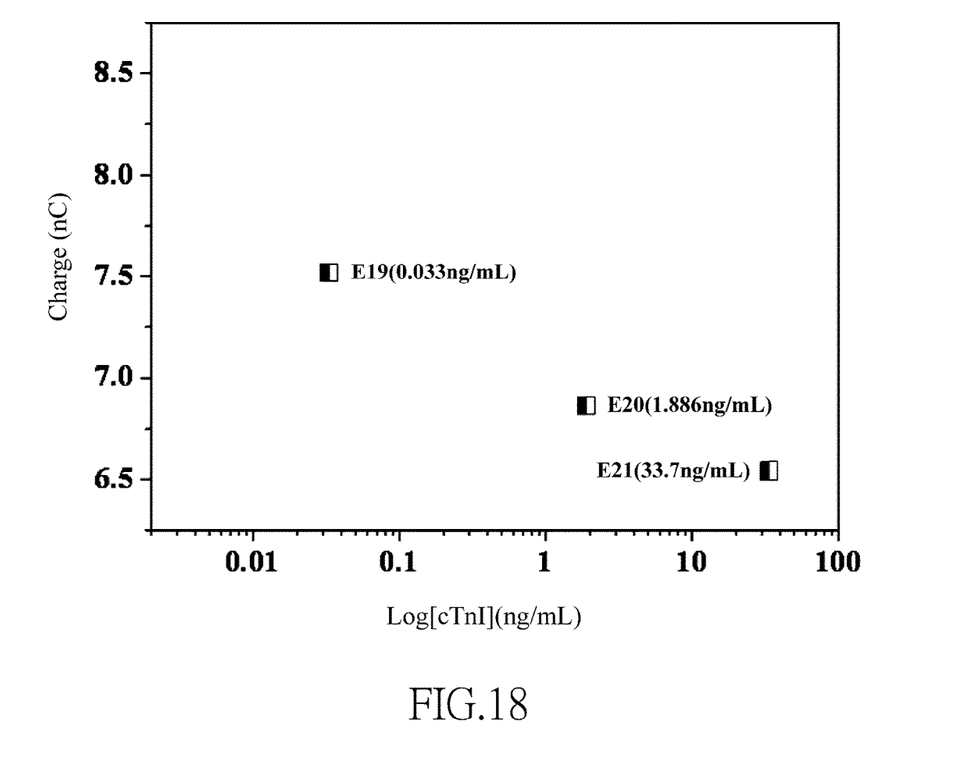
FIG. 18 shows the accumulated charges of Examples 19 to 21 at 50 μs after the application of the voltage pulse with respect to the CVD biomarker concentration in a logarithmic scale.

Integration computational processing on the response currents of Examples 1 to 21 and References 1 and 2 with respect to the voltage applying time was performed by the analyzer (Agilent B1530A) to obtain the amount of total charge accumulated at the biosensor, as correspondingly illustrated in FIGS. 4, 8, 11, 14, and 17. Similar to the response currents, it is shown that the amount of total charge accumulated at the biosensor is correlated to the CVD biomarker concentration in the liquid sample. Specifically, as shown in FIGS. 9, 15 and 18, the total charge accumulated at the biosensor at 50 µs after the application of the voltage pulse are approximately in inverse proportion to the logarithmic CVD biomarker concentration in the liquid sample.

Figure 5:
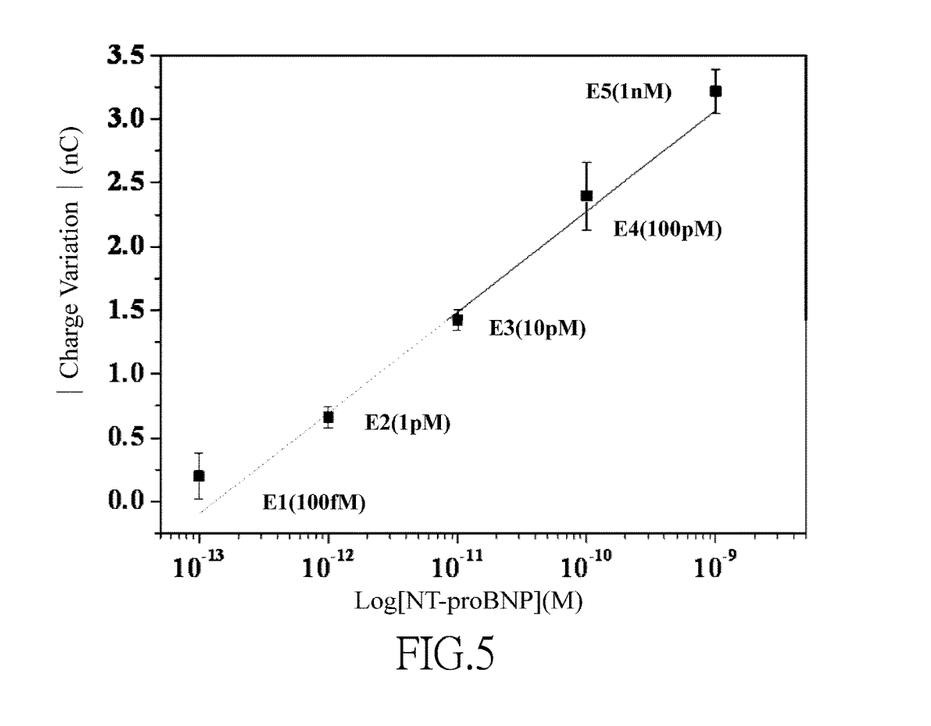
FIG. 5 shows the charge variations between each of Examples 1 to 5 and Comparative Example 1 at 50 μs after the application of a voltage pulse with respect to the CVD biomarker concentration in a logarithmic scale.
Figure 12:
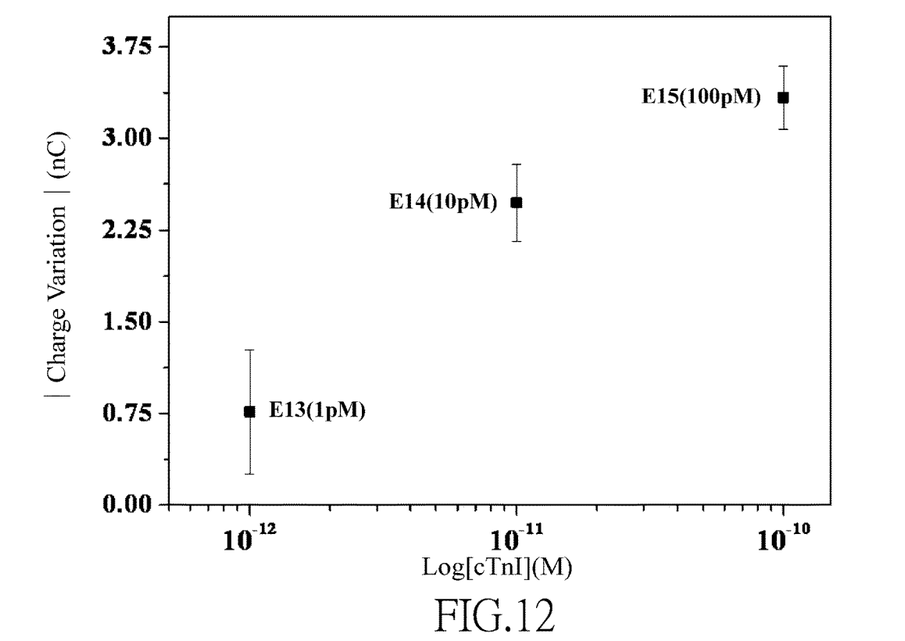
FIG. 12 shows the charge variations between each of Examples 13 to 15 and Comparative Example 2 at 50 μs after the application of the voltage pulse with respect to the CVD biomarker concentration in a logarithmic scale.

In addition, FIG. 5 further shows the accumulated charge variations between each of Examples 1 to 5 and Reference 1, where the total accumulated charge of the Examples 1 to 5 were subtracted by the charge attributed to the response current of Reference 1. The charge variations of Examples 1 to 5 are approximately in proportion to the logarithmic CVD biomarker concentration in the liquid sample. Similarly, FIG. 12 illustrates the accumulated charge variations between each of Examples 13 to 15 and Reference 2 at 50 µs after the application of the voltage pulse and shows the same relationship as depicted by FIG. 5. As such, the charge accumulated at the biosensor within a pulse width of an applied voltage pulse can be another reliable analyzing factor.

It will be apparent, however, to one skilled in the art, that one or more other embodiments maybe practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for analyzing concentration of a cardiovascular disease (CVD) biomarker in a liquid sample, comprising:
    applying the liquid sample to a biosensor, the biosensor including a transistor having a drain, a source, and a gate terminal disposed between the drain and the source, and a reactive electrode spaced apart from the gate terminal, the drain and the source of the transistor, the reactive electrode having a receptor immobilized thereon for specific binding with the CVD biomarker in the liquid sample, the liquid sample being in contact with the gate terminal of the transistor and the reactive electrode;
    applying a voltage pulse between the reactive electrode and the source of the transistor, the voltage pulse having a pulse width;
    monitoring a response current, which is produced in response to the voltage pulse, within the pulse width from the biosensor; and
    analyzing the response current that is correlated to the concentration of the CVD biomarker in the liquid sample.

2. The method of claim 1, wherein the CVD biomarker is Troponin I.

3. The method of claim 1, wherein the CVD biomarker is NT-proBNP.

4. The method of claim 1, wherein the receptor includes an antibody.

5. The method of claim 1, wherein the receptor includes an aptamer.

6. The method of claim 1, wherein the pulse width of the voltage pulse is not greater than $10^{-3}$ second.

7. The method of claim 1, further comprising a step of performing integration computational processing on the response current with respect to at least a certain period in the pulse width.

8. The method of claim 7, wherein the transistor is selected from the group consisting of a high electron mobility transistor (HEMT), a silicon-based transistor, a nanowire transistor, a carbon nanotube (CNT)-included transistor, a graphene transistor, and a molybdenum disulfide ($MoS_2$)-included transistor.

9. The method of claim 1, wherein the reactive electrode and the gate terminal are arranged in a co-planar manner.

10. The method of claim 1, wherein the liquid sample is a blood.

11. The method of claim 1, wherein the liquid sample is a blood serum.

* * * * *